(12) United States Patent
Hossainy (10) Patent No.: US 8,579,956 B2
(45) Date of Patent: Nov. 12, 2013

(54) METHODS AND DEVICES FOR TREATING LESIONS

(75) Inventor: Syed Faiyaz Ahmed Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 455 days.

(21) Appl. No.: 12/239,170

(22) Filed: Sep. 26, 2008

(65) Prior Publication Data

US 2009/0270906 A1 Oct. 29, 2009

Related U.S. Application Data

(60) Provisional application No. 60/976,240, filed on Sep. 28, 2007.

(51) Int. Cl.
*A61F 2/06* (2013.01)

(52) U.S. Cl.
USPC ....... 623/1.11; 606/192; 606/194; 604/96.01; 604/103.08

(58) Field of Classification Search
USPC ............... 606/191, 192, 194, 198; 604/96.01, 604/103.06, 103.07, 103.08, 604/103.01–103.05, 508, 509, 500, 523, 604/536; 623/1.11
See application file for complete search history.

(56) References Cited

U.S. PATENT DOCUMENTS

| | | | | |
|---|---|---|---|---|
| 5,389,314 A * | 2/1995 | Wang | | 264/454 |
| 5,611,775 A * | 3/1997 | Machold et al. | | 604/509 |
| 5,755,722 A * | 5/1998 | Barry et al. | | 606/108 |
| 5,873,852 A * | 2/1999 | Vigil et al. | | 604/509 |
| 5,928,247 A * | 7/1999 | Barry et al. | | 264/171.12 |
| 6,048,332 A * | 4/2000 | Duffy et al. | | 604/103.08 |
| 6,129,700 A * | 10/2000 | Fitz | | 604/30 |
| 6,302,870 B1 * | 10/2001 | Jacobsen et al. | | 604/272 |
| 6,544,221 B1 * | 4/2003 | Kokish et al. | | 604/103.01 |
| 6,638,246 B1 * | 10/2003 | Naimark et al. | | 604/103 |
| 6,695,830 B2 * | 2/2004 | Vigil et al. | | 604/509 |
| 6,808,518 B2 * | 10/2004 | Wellman et al. | | 604/507 |
| 6,991,617 B2 * | 1/2006 | Hektner et al. | | 604/103.01 |
| 2004/0204677 A1 * | 10/2004 | Wellman et al. | | 604/96.01 |
| 2007/0213761 A1 * | 9/2007 | Murphy et al. | | 606/194 |
| 2008/0014276 A1 | 1/2008 | Basu et al. | | |

* cited by examiner

*Primary Examiner* — Gary Jackson
*Assistant Examiner* — Katrina Stransky
(74) *Attorney, Agent, or Firm* — Randy Shen; Blakely Sokoloff Taylor & Zafman LLP (57) ABSTRACT

An method and apparatus are disclosed including an expandable body having a diameter suitable for insertion into a blood vessel and capable of being modified from a first diameter to a second larger diameter in response to an inflation pressure. The expandable body includes an outer wall having a plurality of delivery outlets extending from a working length of the outer wall. The delivery outlets coincide with regions of a lesion exposed between a framework implanted within the vessel when the expandable body is in an expanded state. A treatment agent is delivered from the delivery outlets to regions of the lesion exposed between the implantable framework.

25 Claims, 6 Drawing Sheets

METHODS AND DEVICES FOR TREATING LESIONS

CROSS-REFERENCE TO RELATED APPLICATIONS

This application claims priority from U.S. Provisional Patent Application No. 60/976,240 filed on Sep. 28, 2007, which is incorporated herein by reference in its entirety.

FIELD

Methods and devices for treating lesions.

BACKGROUND

A major component of morbidity and mortality attributable to cardiovascular disease occurs as a consequence of the partial or complete blockage of vessels carrying blood in the coronary or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements often employ surgical techniques that attach natural or synthetic conduits around the occlusion, thereby providing bypass grafts, or employ revascularization by various means to physically enlarge the vascular lumen at the site of occlusion. Significant morbidity and even mortality frequently accompany surgical approaches.

Balloon angioplasty is utilized as an alternative to bypass surgery for treatment early in the development of stenosis or occlusion of blood vessels due to the abnormal build-up of plaque on the endothelial wall of a blood vessel. Angioplasty typically involves guiding a catheter that is usually fitted with a balloon through an artery to the region of stenosis or occlusion, followed by brief inflation of the balloon to push the obstructing intravascular material or plaque against the endothelial wall of the vessel, thereby compressing or breaking apart the plaque and reestablishing blood flow. In some cases, particularly where a blood vessel may be perceived to be weakened, a stent is deployed.

Balloon angioplasty and stent deployment, however, may result in injury to a wall of a blood vessel and its endothelial lining. For example, undesirable results such as denudation (removal) of the endothelial cell layer in the region of the angioplasty, dissection of part of the inner vessel wall from the remainder of the vessel wall with the accompanying occlusion of the vessel, or rupture of the tunica intima layer of the vessel may occur. A functioning endothelial reduces or mitigates thrombogenicity, inflammatory response, and neointimal proliferation.

Attempts to treat or reduce injury to the vessel wall resulting from stent or balloon deployment as well as the ischemia or restenosis to tissue regions resulting from the occlusion have included systemic and local delivery of therapeutics. Systemic delivery, however, has several disadvantages. In particular, in systemic delivery techniques, the whole organism is treated therefore greater amounts of drugs must be supplied which are sometimes toxic to the organism.

Local delivery techniques may be used to overcome some of the disadvantages of systemic delivery techniques, however, a separate set of problems arise. Typically, in local delivery techniques, a treatment agent is injected into a blood stream or healthy vessel region at a point upstream from the treatment site or into an unperfused vessel region after first occluding the vessel region to inhibit blood flow. In either case, otherwise healthy vessel regions are traumatized in order to treat the injured tissue region.

SUMMARY

An apparatus is disclosed. In one embodiment, the apparatus includes an expandable body having a diameter suitable for insertion into a blood vessel and capable of being modified from a first diameter to a second larger diameter in response to an inflation pressure. The expandable body includes an outer wall having a plurality of delivery outlets extending from a working length of the outer wall to coincide with regions of a lesion exposed between a framework implanted within the vessel when the expandable body is in an expanded state. In one embodiment, the expandable body is a balloon and the framework implanted within the vessel is a stent. In one embodiment, the delivery outlets may be flexible needles. Additionally, recesses disposed within the outer wall may serve as delivery outlets.

In another embodiment, a method is disclosed. In one embodiment, the method includes introducing an implantable framework to a point within a vessel lumen coextensive with a lesion. An expandable body is introduced to the point coextensive with the lesion. The expandable body includes an outer wall having a plurality of delivery outlets extending from a working length of the outer wall. A treatment agent may be delivered from the delivery outlets to regions of the lesion exposed between the implantable framework. As used herein, suitable treatment agents include, but are not intended to be limited to, drugs, biologically active agents, chemically active agents, therapeutic agents, and the like, and pharmaceutical compositions thereof, which can be used to deliver a treatment agent to a treatment site as described herein. In some embodiments, the treatment agent may be an agent suitable for local treatment, regional treatment or a combination of agents suitable for local and regional treatment. For example, the treatment agent may be a combination of anti-inflammatory and anti-proliferative agents. In still further embodiments, the treatment agent is an agent that would benefit a damaged blood vessel or an infarcted area. Still further, a contrast agent may be delivered from the delivery outlets in combination with, or in addition to, a treatment agent.

In yet another embodiment, a kit is disclosed. In one embodiment, the kit includes an implantable framework having a first outer diameter suitable for insertion into a blood vessel and a second outer diameter to retain a perimeter similar to that of the blood vessel. The implantable framework may include a plurality of spaces when at the second outer diameter. The kit may further include a cannula having a dimension suitable for insertion into a blood vessel and an expandable body coupled thereto. The expandable body may include an outer wall having a diameter suitable for insertion through the blood vessel. The outer wall may include a plurality of delivery outlets disposed along a working length of the outer wall to coincide with spaces of the framework when the expandable body is in an expanded state. The kit may further include a treatment agent for delivery to a treatment site.

DETAILED DESCRIPTION

The following description provides for techniques for locally and regionally treating a blood vessel by delivering a treatment agent, such as a bioactive formulation, with a delivery device into a lesion. The term "lesion" as used herein refers to any traumatized, diseased or otherwise injured vessel region. In one aspect, the lesion may be, but is not limited to, a vessel region having an occlusion, an atherosclerotic plaque or a vulnerable plaque or a permanent implant.

In one aspect, a stent is implanted and deployed within a vessel region at a position corresponding to a lesion within the blood vessel. The stent is positioned in the blood vessel to radially encompass the lesion. A delivery device including a balloon and delivery outlet, for example a needle, is inserted into the vessel and the balloon inflated at a position within the stent. Upon inflation, the needle may pierce through areas of the lesion exposed between the stent framework to deliver a treatment agent loaded therein. As described, the vessel region at a point including the lesion is injured therefore any additional needle-related injury to the lesion is of no consequence. In this aspect, the delivery techniques and devices described herein allow for treatment of lesions without causing further injury to healthy vessel regions. Still further a local or regional treatment agent or a combination of local and regional treatment agents may be delivered to the vessel such that when the treatment agent is delivered to a region of the vessel wall concentrically outward from the lesion, the treatment agent may travel through the vessel wall tissues to regions of the vessel upstream to the point of delivery and treat the vessel both locally and regionally.

Treatment Agents

In one embodiment, the treatment agent is an anti-inflammatory agent. Examples include, but are not limited to, mometasone, clobetasol and dexamethasone. In another embodiment, the treatment agent is an anti-proliferative agent. Examples of anti-proliferative agents include, but are not limited to, sirolimus, everolimus, zotarolimus, and paclitaxel. In another embodiment, the treatment agent may be a combination of anti-inflammatory and anti-proliferative agents. In still another embodiment, a treatment agent is an agent that would benefit a damaged blood vessel or an infarcted area. In one sense, a treatment agent is an agent that would benefit a blood vessel or an infarcted area (e.g., tissue) by itself creating new cells or new cell components or trigger a repair mechanism. A treatment agent may also include an agent that may benefit a blood vessel or an infarcted area (e.g., tissue) only with the assistance of another exogenous or endogenous agent. In this aspect, suitable treatment agents may include, but are not limited to, growth factors (e.g., vascular endothelial growth factor (VEGF), fibroblast growth factor (FGF), platelet-derived growth factor (PDGF)), cellular components, proteins, cytokines, and drugs. Still further, the treatment agent may include a bioactive agent used to induce regression or slow progress of an atherosclerotic plaque, such as apolipoprotein A1 (Apo A1) or a mutant or mimic form of Apo A1, or a molecule mimicking the cholesterol transporting capacity of ApoA1. The treatment agent may include an agent that inhibits the resorption of bone. Representatively, a suitable agent may be, but is not limited to, bisphosphonate.

In one embodiment, a single treatment agent may be delivered to a desired vessel region. Alternatively, a combination of any number of the above-described treatment agents may be delivered to a desired vessel region. In one embodiment, a combination of a local treatment agent and a regional treatment agent may be selected for delivery to a desired vessel region. A "local treatment agent" as the term is used herein generally refers to a treatment agent suitable for treating an organism at a point of delivery. A "regional treatment agent" as the term is used herein generally refers to a treatment agent suitable for treating an organism at a point distal to a point of delivery, for example a vessel region downstream or upstream from a point of delivery. In this aspect, although a treatment formulation may be injected locally into a lesion, regional treatment, for example, to a vessel region downstream from the lesion, may be achieved by the regional treatment agent. For example, in one embodiment, a combination of everolimus for treatment of restenosis locally and ApoA1 to regionally treat the vessel may be delivered to the lesion. In other embodiments, a mitotic inhibitor such as paclitaxel (local treatment agent) and a bone resorption inhibitor such as bisphosphonate (regional treatment agent) may be combined and delivered to the lesion.

The treatment agent may be delivered to a target region in the form of a solution or formulation. Representatively, the solution may be a saline buffer solution and a treatment agent. The amount of each agent in solution may be any amount sufficient to locally or regionally treat the desired vessel region. In one embodiment, the amount of each agent within the solution may be anywhere from zero to 100 percent weight by volume (w/v). In one embodiment, the solution may include a treatment agent and a contrast agent. In one embodiment, the contrast agent may be a radiopaque material such as a diatrizoate such as RENOGRAFIN™ (Bracco Diagnostics, Inc. of Princeton, N.J.) that may be detected using x-ray. In this aspect, a location of the treatment agent may be determined. Alternatively, the contrast agent may be delivered to a target vessel region separate from the treatment agent.

Carriers

In one embodiment, the treatment agent may be packaged or encapsulated in a carrier. In some embodiments where the solution includes a combination of treatment agents, one of the treatment agents, for example a treatment agent desired to be used for regional treatment of the blood vessel may be packaged in a carrier. Alternatively, a local treatment agent may be encapsulated within a carrier. A carrier may include a matrix that contains one or more treatment agents. A suitable carrier may take the form of a nanoparticle (e.g., nanosphere), microparticle (e.g., microsphere), liposome, and the like particles, as the situation may dictate. For example, the carrier may be a liposome or other outer shell such as, for example, lipid or polymer membranes, polymer shells, or other lipidphilic shells. A suitable material for the carrier may be a polypropylene sulfide (PPS).

In one aspect, the carrier may be a sustained-release carrier. Suitable materials for sustained-release carriers may include, but are not limited to, encapsulation polymers such as poly (L-lactide), poly (D,L-lactide), poly (glycolide), poly (lactide-co-glycolide), polycaprolactone, polyanhydride, polydioxanone, polyorthoester, polyamino acids, or poly (trimethylene carbonate), and combinations thereof.

The carrier may provide for release of the treatment agent for a period of time sufficient to achieve a desired effect at the desired treatment region. It is further contemplated that sustained release microparticle formulations with different release rates may be delivered in combination to achieve multi-modal release profiles over a period of time.

In one exemplary embodiment, a formulation including a treatment agent encapsulated in a carrier may include everolimus encapsulated in PPS nanoparticles of 100 nanometer diameter and ApoA1 encapsulated in a 1,2-distearoyl phosphatidylcholine (DSPC)-based liposome. A medium for the carrier may be PBS or 0.05% Hyaluronic acid in phosphate-buffered saline (PBS).

To form a sustained-release carrier composition of, for example, microparticles or nanoparticles (e.g., microspheres or nanospheres) or liposomes comprising one or more treatment agents or a modified carrier surface, the following techniques may be used.

1. Solvent Evaporation:

In this method, the polymer is dissolved in a volatile organic solvent such as methylene chloride. The treatment agent is then added to the polymer solution either as an aqueous solution containing an emulsifying agent such as polyvinyl alcohol (PVA), or as a solid dispersion, and stirred, homogenized or sonicated to create a primary emulsion of protein in the polymer phase. This emulsion is stirred with an aqueous solution containing an emulsifying agent such as PVA to create a secondary emulsion of treatment agent containing polymer in the aqueous phase. This emulsion is stirred in excess water, optionally under vacuum to remove the organic solvent and harden the particles. The hardened particles are collected by filtration or centrifugation and lyophillized. A desired particle size (e.g., microparticle or nanoparticle) is selected by varying the preparation conditions (e.g., viscosity of the primary emulsion, concentration of the treatment agent, mixing (shear) rate, etc.). The particles tend to adopt a spherical shape in response to minimizing surface tension effects.

2. Coacervation:

In this method, a primary emulsion of treatment agent in an aqueous phase is formed as in the solvent evaporation method. This emulsion is then stirred with a non-solvent for the polymer, such as silicone oil to extract the organic solvent and form embryonic particles of polymer with trapped treatment agent. The non-solvent is then removed by the addition of a volatile second non-solvent such as heptane, and the particles hardened. The hardened particles are collected by filtration or centrifugation and lyophilized. Again, the particle size is selected as described above with reference to solvent evaporation.

3. Spray Drying:

In this method, a treatment agent, formulated as lyophilized powder is suspended in a polymer phase consisting of polymer dissolved in a volatile organic solvent such as methylene chloride. The suspension is then spray dried to produce polymer particles with entrapped treatment agent. The particle size is selected as described above with reference to solvent evaporation.

4. Cryogenic Process:

In this method, the treatment agent formulated as lyophilized powder is suspended in a polymer phase consisting of polymer dissolved in a volatile organic solvent such as methylene chloride. The suspension is sprayed into a container containing frozen ethanol overlaid with liquid nitrogen. The system is then warmed to −70° C. to liquefy the ethanol and extract the organic solvent from the treatment agent particles. The hardened microspheres are collected by filtration or centrifugation and lyophilized.

5. Electrospraying:

In this method, a solution including a treatment agent, a biodegradable polymer and a solvent is formed. The solution is passed through an electrocharged nozzle and onto a collection assembly. A grounded electrode is positioned proximal to the collection assembly and used to attract the electrocharged solution to the collection assembly. The solvent then evaporates from the particulate solution to form particles having the treatment agent encapsulated within. The method described herein is similar in certain respects to the methods described in commonly-owned, co-pending, U.S. patent application Ser. No. 11/485,934 filed on Jul. 12, 2006 of Basu et. al. titled Methods and Devices for Forming Treatment Agent Carriers.

6. Example of Loading and Dose

As noted above, one example of the preparation of nanoparticles (e.g., nanospheres) or microparticles (e.g., microspheres) suitable for use in therapeutic angiogenesis is in the form of a solution. The solution may include any amount of the treatment agent found to have a desired effect at a desired treatment site. Representatively, the treatment agent may make up between zero percent and 100 percent of the solution by volume. Still further, where the solution includes a regional treatment agent and a local treatment agent, the regional treatment agent and the local treatment agent combined may be between zero percent and 100 percent of the solution by volume. Nanoparticles or microparticles may be loaded with a desired treatment agent in the range of about 0.5 to about 30 percent w/v as deemed desirable.

Delivery Devices

Figure 1:
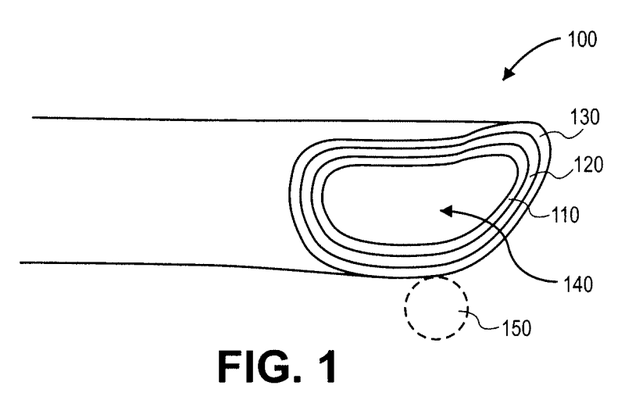
FIG. 1 shows a schematic side and sectional view of a blood vessel.

Referring to FIG. 1, a non-diseased artery is illustrated as a representative blood vessel. Blood vessel 100 includes an arterial wall having a number of layers. Inner most layer 110 represents the intimal layer which includes the endothelium, the subendothelial layer, and the internal elastic lamina. Medial layer 120 is concentrically outward from inner most layer 110 and bounded by external elastic lamina. There is no external elastic lamina in a vein. Medial layer 120 (in either an artery or vein) primarily consists of smooth muscle fibers and collagen. Adventitial layer 130 is concentrically outward from medial layer 120. The arterial wall (including inner most layer 110, medial layer 120 and adventitial layer 130) defines lumen 140 of blood vessel 100. Adventitial layer 130 lies radially inward from a peri-adventitial space 150. Areas radially outward from peri-adventitial space 150 include connective tissue such as adipose tissue and muscle tissue. Stenosis or occlusion of a blood vessel typically occurs by the build-up of plaque on inner most layer 110 and can result in decreased blood flow through lumen 140. One technique to address this is balloon angioplasty and stent deployment. As previously discussed, however, balloon angioplasty and stent deployment may result in further injury to a wall of a blood vessel and its endothelial lining.

Delivery of a treatment agent, such as an immunosuppressant, to the already injured vessel region (e.g. after stent deployment) as described herein provides a technique in which the injured vessel region may be treated without further injury to nearby healthy regions. In one embodiment, the treatment agent may be delivered to a desired region of a vessel wall by injecting it into a region of a lesion accessible through the walls of a deployed stent. Such delivery may be achieved using a medical device including an expandable body, such as a balloon, having needles arranged along an outer perimeter of the body that are folded along the outer perimeter of the body before deployment of the needles while positioning the medical device. In other embodiments, the body may contain recesses along its outer perimeter. Alternatively or additionally, the balloon may be protected by a sheath that may be retracted once the balloon is positioned at a desired location in the blood vessel. Once the device is positioned at the desired region, injected fluid may be used to inflate the balloon from a first diameter to a second, larger diameter and in turn cause the needles to unfold and puncture lesion regions exposed between the stent struts or walls. The needles may be flexible allowing for crimping a stent onto the balloon without damaging the needles.

Figures 2, 3:
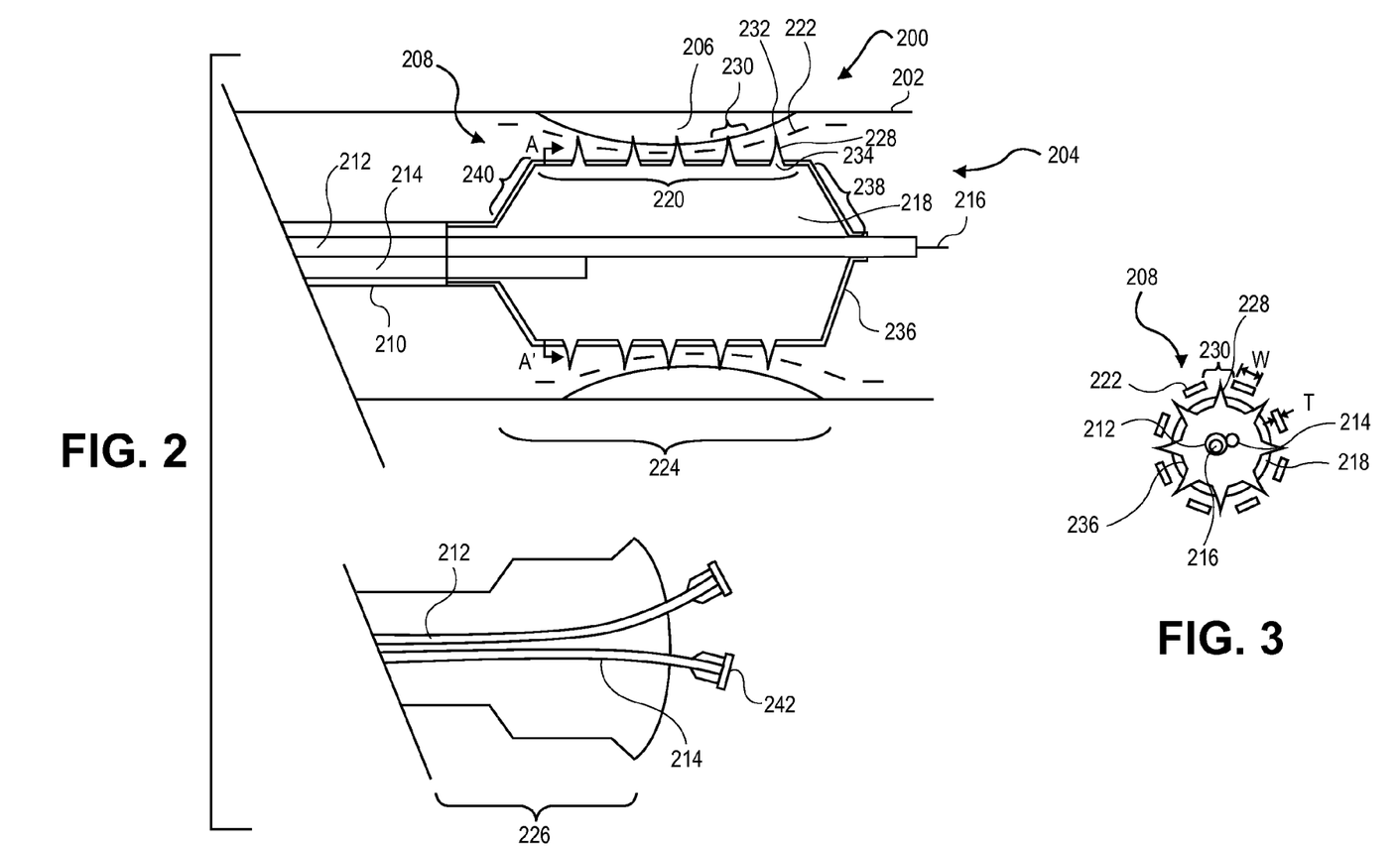
FIG. 2 shows a cross-sectional schematic side view of a blood vessel including a lesion and having one embodiment of a device including a stent and balloon within the blood vessel.
FIG. 3 shows a cross-sectional side view of the device of FIG. 2 through line A-A'.

FIG. 2 shows a cross-sectional schematic side view of a blood vessel including an occlusion and an embodiment having a stent and a balloon disposed in the blood vessel. Referring to FIG. 2, blood vessel 200 includes blood vessel wall 202 defining lumen 204. Disposed within blood vessel 200 is a lesion 206. Lesion 206 modifies the cross-sectional shape of lumen 204 from generally circular to irregular or oblong.

FIG. 2 shows a device disposed within lumen 204. In one embodiment, the device may include an expandable body and an implantable framework. The implantable framework may be a stent 222, and the expandable body may be a balloon of a catheter assembly 208. FIG. 2 shows a distal portion 224 and a proximal portion 226 of catheter assembly 208. Proximal portion 226 may be outside of the blood vessel 200 and the patient. Representatively, stent 222 and catheter assembly 208 may enter the patient percutaneously, such as through a femoral artery and through, for example, a guide catheter with the aid of a guidewire to a location in the vasculature. That location may be, for example, a coronary artery. In one embodiment, stent 222 may be mounted on a balloon 218 of catheter assembly 208 during insertion. FIG. 2 shows distal portion 224 of catheter assembly 208 positioned adjacent lesion 206. Catheter assembly 208 includes primary cannula 210 having a lumen therethrough. The lumen contains at least a guidewire cannula 212 and inflation cannula 214. Each of guidewire cannula 212 and inflation cannula 214 has a lumen therethrough. A lumen of guidewire cannula 212 accommodates guidewire 216. Catheter assembly 208 also includes balloon 218 connected at a proximal end to primary cannula 210 and at a distal end to guidewire cannula 212. A distal end of inflation cannula 214 is disposed within balloon 218 such that balloon 218 fluidly communicates with inflation cannula 214, formed within primary cannula 210 of catheter assembly 208.

In the embodiment shown in FIG. 2, balloon 218 includes balloon wall or membrane 236, which is selectively inflatable from a collapsed configuration (first diameter) to a desired and controlled expanded configuration (second diameter). Balloon 218 can be selectively inflated by supplying a fluid into inflation cannula 214 at a predetermined rate or pressure through inflation port 242. Balloon 218 is selectively deflatable, after inflation, to return to the collapsed configuration or a deflated profile. In one embodiment, balloon wall 236 can be defined by three sections, distal taper wall 238, medial working length 220, and proximal taper wall 240. As shown in FIG. 2, balloon 218 is positioned, in one embodiment, such that working length 220 is positioned adjacent a length of lesion 206. In one embodiment, proximal taper wall 240 and distal taper wall 238 can taper at any suitable angle θ, typically between about 10° to less than about 90°, when balloon 218 is in the expanded configuration.

Distal taper wall 238, medial working length 220, and proximal taper wall 240 may be bound together by seams or be blown molded out of a single seamless material. Balloon 218 may be made from any suitable material, including, but not limited to, polymers and copolymers of polyolefins, polyamides, polyesters and the like. The specific material employed must be mutually compatible with the fluids employed in conjunction with balloon 218 and must be able to withstand the pressures that are developed within balloon 218. In one embodiment, balloon wall 236 may have any suitable thickness so long as the thickness does not compromise properties that are critical for achieving desired performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness may be in the range of about 10 microns to about 30 microns, the diameter of balloon 218 in the expanded configuration may be in the range of about two millimeters (mm) to about 10 mm, and the length may be in the range of about 3 mm to about 40 mm. It is appreciated that these specifications may vary depending on the procedure for which balloon 218 is to be used and the anatomy and size of the target lumen in which balloon 218 is to be inserted. For example, in one embodiment, working length 220 of balloon 218 has a length dimension similar to that of lesion 206. In other embodiments, the working length of balloon 218 may have a length dimension longer than or shorter than lesion 206. Still further, as will be discussed more fully in reference to FIGS. 4-8, balloon 218 may have more than one wall or more than one recess disposed along a wall and therefore have, for example, a material or wall thickness different from that which is described above.

Liquids containing treatment agents, diagnostic agents (contrast) or a combination of treatment and diagnostic agents may also be used to inflate balloon 218. In one embodiment, balloon 218 may be made of a material that is permeable to such therapeutic or diagnostic liquids. To inflate balloon 218, the fluid may be supplied into inflation lumen 214 at a predetermined pressure, for example, between about one atmosphere (atm) and 20 atm.

Overlying working length 220 of balloon 218 is stent 222. In this embodiment, stent 222 is mounted on a distal portion of catheter assembly 208. Stent 222 may be a generally tubular stent including a plurality of radially expandable cylindrical elements such as a plurality of struts disposed generally coaxially and interconnected by connecting elements and a plurality of links disposed between adjacent struts. It is contemplated that stent 222 can be any standard bare stent (non-coated), drug-eluting stent (DES) or a coated stent. Materials used to make stent 222 can include, but are not limited to, cobalt, chromium (CoCr) alloy, cobalt alloy, nickel alloy, titanium alloy, nickel titanium alloy, stainless steel, or other corrosion resistant alloy. Still further, stent 222 can be made of a bioabsorbable material such as a biodegradable polymeric compound, including polymers of lactic acid, poly (alpha-hydroxy acid) such as poly-L-lactide (PLLA), poly-D-lactide (PDLA), polyglycolide (PGA), polydioxanone, polyglycolic acids, polycaprolactone, polygluconate, polylactic acid-polyethylene oxide copolymers, modified cellulose, collagen, poly(hydroxybutyrate), polyanhydride, polyphosphoester, poly(amino acids), tyrosine-derived polycarbonates, poly-lactic-co-glycolide (PLGA) or related copolymers, as well as blends of the foregoing polymers, or their respective monomers, dimers, or oligomers, each of which have a characteristic degradation rate in the body.

Stent 222 may be expanded upon inflation of underlying balloon 218 at a substantially low pressure to prevent unnecessary trauma or injury to the vessel. In one embodiment, stent 222 may be deployed at a pressure of between about 8 atm to about 10 atm, in some embodiments between about 8 atm and 15 atm. In still further embodiments, a pressure lower than at least about 6 atm, in some embodiments, lower than about 3 atm, and in some other embodiments, even lower than about 1 atm may be used to deploy stent 222. In this aspect, stent 222 need only to oppose the inner wall of artery 200 over the vulnerable plaque section but need not support vessel 200 or apply excessive force to open artery 200.

Returning to balloon 218 of catheter assembly 208, balloon 218 has a plurality of delivery outlets 228 disposed along working length 220 of balloon 218. As illustrated in FIG. 2, delivery outlets 228 are positioned such that they coincide with openings 230 between the struts and links of stent 222 when balloon 218 is inflated. In this aspect, delivery outlets 228 may be spaced along balloon 218 a distance apart which is greater than the width of the struts or links. In this aspect, delivery outlets 228 populate openings 230 between struts and links of stent 222 when balloon 218 is expanded. Alternatively, delivery outlets 228 can be disposed anywhere and according to any pattern along working length 220 of balloon 218 so long as at least one delivery outlet 228 coincides with at least one opening 230.

In one embodiment, delivery outlets 228 may be needles extending from a surface of balloon 218. In one embodiment, needles 228 may be inserted through an inner surface of outer wall 236 of balloon 218 a distance such that one end of needle 228 remains in fluid communication with delivery cannula 214 and another end of needle 228 extends from an outer surface of balloon wall 236. Alternatively, needles 228 may be secured with an adhesive to needle apertures preformed in wall 236 such that a lumen of each needle 228 is aligned with an aperture. In one embodiment, needles 228 may be made of a flexible material so that stent 222 may be crimped onto balloon 218 before deploying stent 222 without damaging needles 228. Representatively, needles 228 may be made of a flexible material such as, but not limited to, a low-density polyethylene, polyurethane and polyvinyl chloride (PVC). In other embodiments, needles 228 may be made of any material suitable for puncturing lesion 206 or vessel wall 202 and delivering a treatment agent, such as, for example, a metal, metal alloy, silicon or glass material.

Needles 228 may include an outlet port 232 on one end of a lumen (not shown) within needle 228 and an inlet port 234 on another end open to an inner surface of balloon wall 236. In this aspect, a fluid released within balloon 218 from inflation lumen 214 may be delivered through needle 228.

In one embodiment, needle 228 may have any dimensions suitable for puncturing lesion 206 of vessel 200 or vessel wall 202 without disrupting lesion 206 (e.g. rupturing a vulnerable plaque). Representatively, needle 228 may have a lumen with a diameter of, for example, 10 µm to about 100 µm and an outer diameter of about 11 µm to about 101 µm. Needle 228 is a length of about 200 µm to about 1500 µm. It is contemplated that a length of needle 228 may vary depending upon various factors, such as the region where treatment agent delivery is desired. For example, in embodiments where needle 228 is about 200 µm long, needle 228 extends into a medial layer of blood vessel 200 when advanced through a wall of blood vessel 200. Alternatively, where needle 228 has a length of about 1500 µm, it extends into a peri-adventitial space when advanced through a wall of blood vessel 200. In still further embodiments, it is contemplated that when a plurality of needles 228 are affixed to balloon 218, the needles can have the same or different lengths. For example, some of the needles are 200 µm while some of the needles are 1500 µm. In this aspect, a treatment agent may be delivered from the needles to both the medial layer and the peri-adventitial space.

Although in FIG. 2 needles 228 are shown piercing only into lesion 206, it is further contemplated that needles 228 may be of a length and diameter to pierce through vessel wall 202 when balloon 218 is expanded. In this aspect, needle 228 may pierce through wall 202 and into, for example, the adventitial layer or peri-advential space concentrically outward from the advential layer. In this aspect, a fluid, such as a treatment agent, released from needle 228 within or adjacent to lesion 206 (e.g. adventitial tissue or peri-adventitial space) may provide local treatment at the lesion site and may further be absorbed by tissues of vessel wall 202 or the peri-advential space and diffuse through the tissues over time to regionally treat vessel regions upstream or downstream from lesion 206.

FIG. 3 shows a cross-sectional side view of catheter assembly 208 at line A-A' of FIG. 2. FIG. 3 illustrates stent 222 having struts overlying balloon 218. A representative strut width, W, for a typical stent is on the order of about 0.0018 inches to about 0.0035 inches. A representative thickness, T, for a typical strut is on the order of about 0.002 inches to about 0.010 inches. Balloon 218 is shown in an expanded configuration having guidewire cannula 212, guidewire 216 and inflation cannula 214 disposed therein. As shown in FIG. 3, needles 228 are positioned along balloon 218 such that when balloon 218 is in an expanded configuration as shown, needles 228 extend through openings 230 between the struts of stent 222. In this aspect, needles 218 may deliver a fluid, such as a treatment agent, to a lesion or vessel wall concentrically outward from stent 222. Although eight needles 228 are illustrated in FIG. 3, it is contemplated that any number of needles extends along working length 220 of balloon 218. Therefore, more than eight needles 228 protrude between openings 230 when balloon 218 is expanded. Still further, the needles may be arranged along balloon 218 in any manner so long as a sufficient number of needles 228 extend between openings 230 to deliver a sufficient amount of a treatment agent to the desired region upon the balloon's 218 expansion. For example, in some embodiments, half of the needles extending from balloon 218 may be beneath struts of stent 222 and half of the needles may extend through openings 230 when balloon 218 is expanded.

Figures 4, 5:
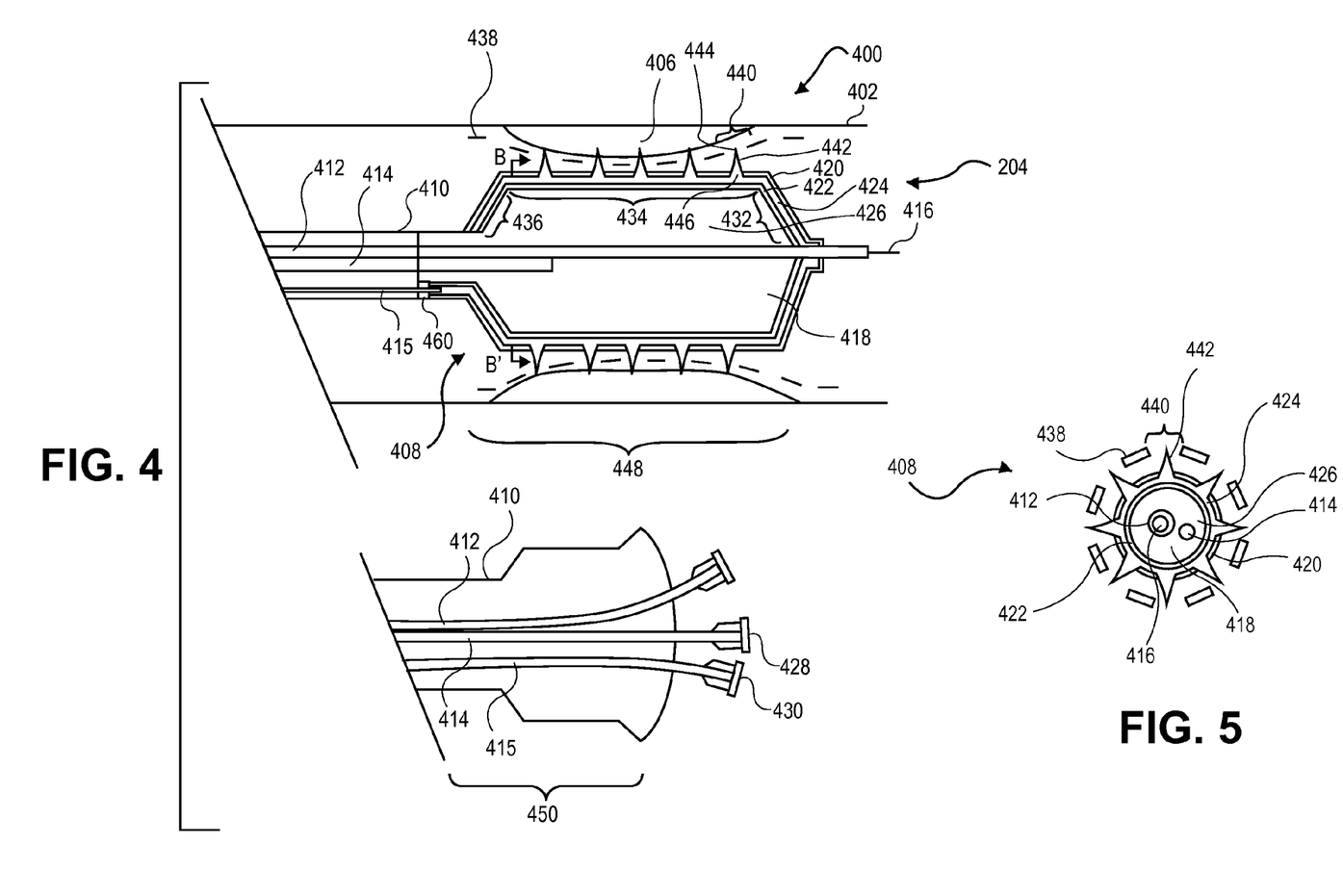
FIG. 4 shows a cross-sectional schematic side view of a blood vessel including a lesion and having another embodiment of a device including a balloon and a stent disposed in the blood vessel.
FIG. 5 shows a cross-sectional side view of the medical device of FIG. 4 through line B-B'.

FIG. 4 shows a cross-sectional schematic side view of a blood vessel including an occlusion and having another embodiment of a device including a balloon and a stent disposed in the blood vessel. Referring to FIG. 4, blood vessel 400 includes blood vessel wall 402 defining lumen 404. Disposed within blood vessel 400 is a lesion 406.

FIG. 4 shows a device disposed within lumen 404 defined by blood vessel wall 402. In one embodiment, the device may include a stent 438 and a balloon catheter assembly 408. A Proximal portion 450 of catheter assembly 408 may be external to blood vessel 400 and to the patient. Representatively, stent 438 and catheter assembly 408 may be inserted through a femoral artery and through, for example, a guide catheter and with the aid of a guidewire to a location in the vasculature of a patient. That location may be a coronary artery. In one embodiment, stent 438 may be mounted on a balloon 418 of catheter assembly 408 during insertion. FIG. 4 shows distal portion 448 of catheter assembly 408 positioned adjacent lesion 406. Catheter assembly 408 includes primary cannula 410 having a lumen therethrough, the lumen sized to contain at least a guidewire cannula 412, a first inflation cannula 414 and a second inflation cannula 415. Each of guidewire cannula 412, first inflation cannula 414 and second inflation cannula 415 has a lumen therethrough. A lumen of guidewire cannula 412 accommodates guidewire 416. Catheter assembly 408 also includes balloon 418 connected at a proximal end to primary cannula 410 and a distal end to guidewire cannula 412.

In the embodiment shown in FIG. 4, balloon 418 is a double walled balloon including an outer balloon wall or membrane 420 and an inner balloon wall or membrane 422. In this aspect, an outer reservoir 424 is formed between outer wall 420 and inner wall 422 and an inner reservoir 426 separate from outer reservoir 424 is defined by inner wall 422. Outer wall 420 and inner wall 422 are attached at one end to a cuff 460 to help maintain separation between outer wall 420 and inner wall 422 so that a distal end of second inflation cannula 415 may be inserted between walls 420, 422 and terminate within outer reservoir 424. In one embodiment, cuff 460 may have a cylindrical shape and be of any material suitable for maintaining an opening defined by walls 420, 422 for insertion of second inflation cannula 415. In this aspect, a distal end of second inflation cannula 415 terminates within outer reservoir 424 and a distal end of first inflation cannula 414 terminates within inner reservoir 426 of balloon 418.

Balloon 418 is selectively inflatable to expand from a collapsed configuration to a desired and controlled expanded configuration. Balloon 418 can be selectively expanded by supplying a fluid into first inflation cannula 414 at a predetermined rate, to create a pressure, through inflation port 428. Alternatively, supplying a fluid into second inflation cannula 415 to a predetermined pressure through inflation port 430 can be selectively expand balloon 418. In still further embodiments, balloon 418 may be selectively expanded by simultaneously supplying a first fluid into first inflation cannula 414 and a second fluid into second inflation cannula 415 to predetermined pressures through fluid ports 428 and 430 respectively. Balloon 418 is selectively deflatable to return to its collapsed configuration or to a deflated profile. In one embodiment, balloon walls 420, 422 can be defined by three sections, distal taper wall 432, medial working length 434, and proximal taper wall 436. As shown in FIG. 4, balloon 418 of catheter assembly 408 is positioned, in one embodiment, such that working length 434 adjoins a length of lesion 406. In one embodiment, proximal taper wall 436 and distal taper wall 432 taper at any suitable angle θ, typically between about 10° to about 90°, when balloon 418 expanded.

Distal taper wall 432, medial working length 434, and proximal taper wall 436 of wall 420 may be bound together by seams or be blow-molded of a single seamless material. Similarly, distal taper wall 432, medial working length 434, and proximal taper wall 436 of wall 422 may be bound together by seams or be blow-molded out of a single seamless material. Wall 420 and wall 422 may be connected at proximal ends to primary cannula 410 and at distal ends to guidewire cannula 412. Balloon 418 may be made from any suitable material, including, but not limited to, polymers and copolymers of polyolefins, polyamides, polyesters and the like. A suitable material for balloon 418 can further include a nylon material.

The specific material employed must be compatible with the fluids employed in conjunction with balloon 418 and must be able to stand the pressures that are developed within balloon 418.

In one embodiment, balloon wall 420 and balloon wall 422 may be made of the same material. Alternatively, balloon wall 420 and balloon wall 422 may be made of different materials. For example, in one embodiment, balloon wall 420 is made of a polymeric material and balloon wall 422 is made of a nylon material. Balloon walls 420, 422 may have any thickness so long as the thickness does not unduly compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, the thickness of each wall 420, 422 may be in the range of about 10 μm to about 30 μm, an outer diameter of balloon 418 in the expanded configuration may be in the range of about 2 mm to about 10 mm, and a length of outer wall 420 may be in the range of about 3 mm to about 40 mm. An outer diameter and length of inner wall 422 may be less than that of outer wall 420 such that a space is provided for outer reservoir 424 formed between outer wall 420 and inner wall 420. Representatively, where an outer diameter of wall 420 is 10 mm and a length is 40 mm, an outer diameter of wall 422 in the expanded configuration may be 8 mm and the length may be 38 mm. It is appreciated that the specific specifications may vary depending on the procedure for which balloon 418 is to be used and the anatomy and size of the target lumen in which balloon 418 is to be inserted. For example, in one embodiment, it may be desirable to have different expansion characteristics for inner reservoir 426 and outer reservoir 424. In this aspect, inner wall 422 and outer wall 420 may have different thicknesses or be made of different materials.

Balloon 418 may be inflated by introducing liquid into first inflation cannula 414 or second inflation cannula 415. Liquids containing treatment or diagnostic agents (e.g. contrast) may also be used to inflate balloon 418. In one embodiment, balloon 418 may be made of a material that is permeable to such therapeutic or diagnostic liquids. To inflate balloon 418, the fluid may be supplied into first inflation lumen 414 or second inflation lumen 415 at a predetermined pressure, for example, between about one and 20 atmospheres.

Overlying working length 434 of balloon 418 is stent 438. In this embodiment, stent 438 is mounted on a distal portion 448 of catheter assembly 408. Stent 438 may be a tubular stent, such as that described in reference to FIG. 2, including a plurality of radially expandable cylindrical elements such as a plurality of struts disposed generally coaxially and interconnected by connecting elements and links disposed between adjacent struts. Stent 438 may be expanded upon inflation of underlying balloon 418 at a pressure as described in reference to FIG. 2 such that stent 438 opposes the inner wall of artery 400 over lesion 406, but it need not support vessel 400 or apply excessive force to open artery 400.

Returning to balloon 418 of catheter assembly 408, balloon 418 has a plurality of delivery outlets 442 disposed along working length 434 of balloon 418. As illustrated in FIG. 4, delivery outlets 442 are positioned similar to that which is described in reference to FIGS. 2 and 3. That is, they coincide with openings 440 between the struts and links of stent 438 when balloon 418 is inflated. In this aspect, delivery outlets 442 populate openings 440 between struts and links of stent 438 when balloon 418 is expanded. Alternatively, delivery outlets 442 may be disposed anywhere along working length 434 of balloon 418 so long as they coincide with at least some of openings 440.

In one embodiment, delivery outlets 442 may be needles extending from a surface of balloon 418. In one embodiment, needles 442 may be inserted through an inner surface of outer wall 420 of balloon 418 a distance such that an end of needle 442 remains within outer wall 420. Alternatively, needles 442 may be secured with an adhesive to needle apertures preformed in outer wall 420 such that a lumen of needles 442 is aligned with the aperture. Needles 442 may include an outlet port 444 on one end of the lumen (not shown) within needle 442 and an inlet port 446 on another end open to outer reservoir 424. In this aspect, a fluid released within outer reservoir 424 from second inflation lumen 415 may be delivered to vessel 400 via needle 442. Needles 442 may be flexible microneedles made of materials and having dimensions similar to those discussed with respect to FIG. 2. In one embodiment, a liquid solution including a treatment agent may be introduced into second inflation cannula 415 and delivered to lesion 406 through needles 442 while a contrast solution may be introduced into first inflation cannula 414 to expand inner reservoir 426 of balloon 418. Alternatively, a liquid solution including a treatment agent and contrast may be introduced into second inflation cannula 415 and delivered to lesion 406 through needles 442 and a contrast solution may be introduced into first inflation cannula 414 to expand inner reservoir 426 of balloon 418. In this aspect, the location of the device may be monitored by viewing contrast within the device with an x-ray. Alternatively, a solution of contrast and treatment agent may be introduced into second inflation cannula 415 and anther liquid solution, for example saline, may be introduced into first inflation cannula 414 to inflate balloon 418. In this aspect, the contrast and treatment agent solution is delivered to lesion 406 so that movement of the treatment agent may be monitored.

FIG. 5 shows a cross-sectional side view of the device of FIG. 4 through line B-B'. FIG. 5 illustrates stent 438 having struts overlying balloon 418. Dimensions of the struts of stent 438 are substantially similar to those described in reference to FIG. 3. Balloon 418 is shown in an expanded configuration having guidewire cannula 412, guidewire 416 and first inflation cannula 414 disposed therein. Needles 442 are positioned along balloon 418 such that when balloon 418 is in an expanded configuration, needles 442 extend through openings 440 between the struts of stent 438. In this aspect, needles 418 may deliver a fluid, such as a treatment agent, to a lesion or vessel wall concentrically outward from stent 438. Needles 442 may be attached to outer wall 420 and in fluid communication with outer reservoir 424 formed between outer wall 420 and inner wall 422. Inner reservoir 426 is defined by inner wall 422. Although eight needles 442 are illustrated, it is contemplated that any number of needles extends along working length 434 of balloon 418 therefore more than eight needles 442 protrude between openings 440 when balloon 418 is expanded. Still further, the needles may be arranged along balloon 418 in any manner so long as a sufficient number of the needles to deliver an effective amount of treatment agent to a desired vessel region extends between stent openings 440 when balloon 418 is expanded.

Figures 6, 7:
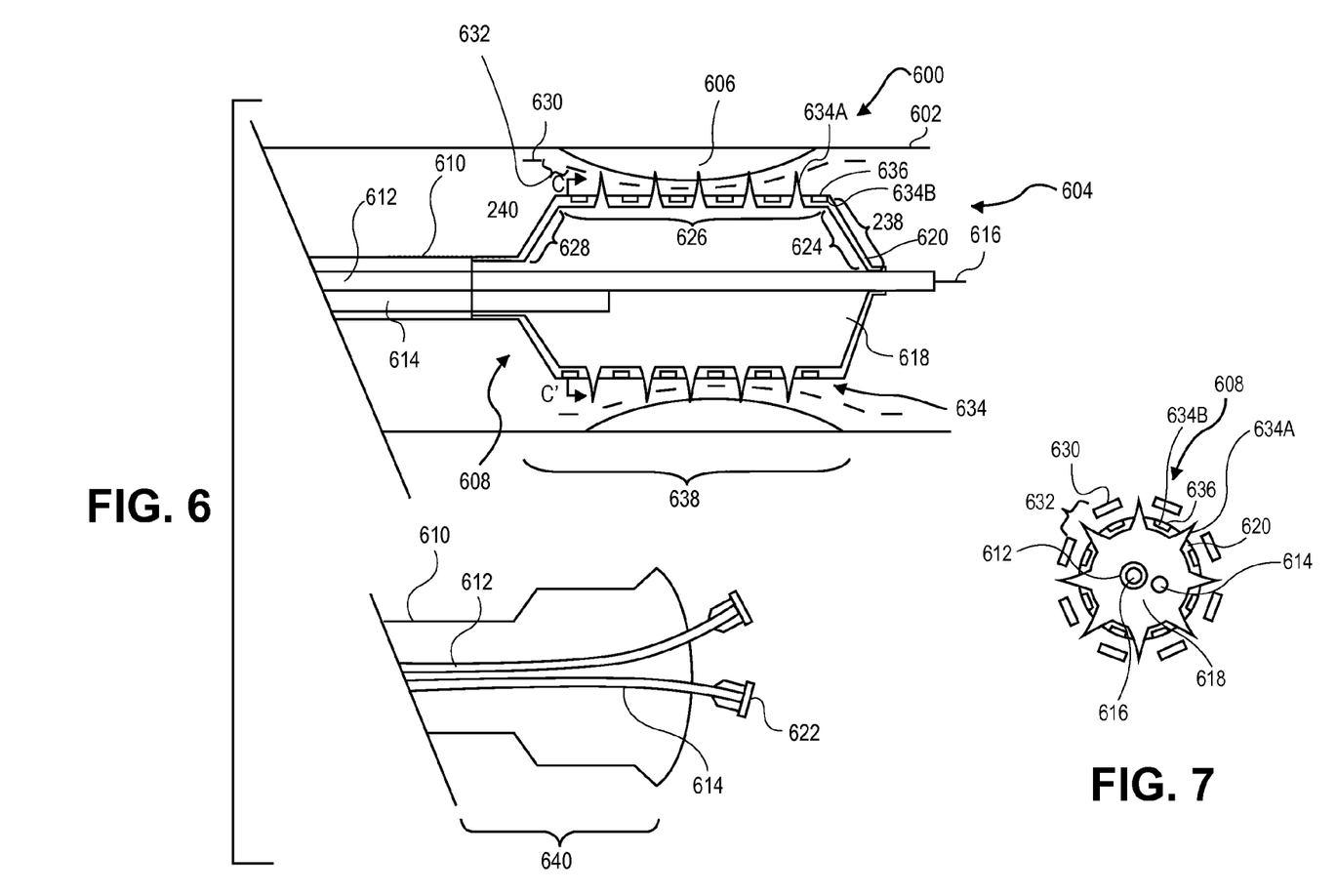
FIG. 6 shows a cross-sectional schematic side view of a blood vessel including a lesion and having another embodiment of a device including a balloon and a stent disposed in the blood vessel.
FIG. 7 shows a cross-sectional side view of the device of FIG. 6 through line C-C'.

FIG. 6 shows a cross-sectional schematic side view of a blood vessel including a lesion and having another embodiment of a device including a balloon and a stent disposed in the blood vessel. Referring to FIG. 6, blood vessel 600 includes blood vessel wall 602 defining lumen 604. Disposed within blood vessel 600 is a lesion 606.

FIG. 6 shows a device disposed within lumen 604 defined by blood vessel wall 602. In one embodiment, the device may include a stent 630 and a balloon catheter assembly 608. FIG. 6 shows a distal portion 638 and a proximal portion 640 of catheter assembly 608. Proximal portion 640 may be external to blood vessel 600 and to the patient. Representatively, stent 630 and catheter assembly 608 may be inserted through a femoral artery and through, for example, a guide catheter and with the aid of a guidewire to a location in the vasculature of a patient. That location may be, for example, a coronary artery. In one embodiment, stent 630 may be mounted on a balloon 618 of catheter assembly 608 during insertion. FIG. 6 shows distal portion 638 of catheter assembly 608 positioned adjacent lesion 606. Catheter assembly 608 includes primary cannula 610 having a lumen therethrough, the lumen sized to contain at least a guidewire cannula 612 and inflation cannula 614. Each of guidewire cannula 612 and inflation cannula 614 has a lumen therethrough. A lumen of guidewire cannula 612 accommodates guidewire 616. Catheter assembly 608 also includes balloon 618 connected at a proximal end to primary cannula 610 and a distal end to guidewire cannula 612. A distal end of inflation cannula 614 is disposed within balloon 618 such that balloon 618 is in fluid communication with inflation cannula 614 within primary cannula 610 of catheter assembly 608.

In the embodiment shown in FIG. 6, balloon 618 includes balloon wall or membrane 620, which is selectively inflatable to expand from a collapsed configuration to a desired and controlled expanded configuration. Balloon 618 can be selectively expanded by supplying a fluid into inflation cannula 614 at a predetermined rate of pressure through inflation port 622. Balloon wall 618 is selectively deflatable, after inflation, to return to the collapsed configuration or a deflated profile. In one embodiment, balloon wall 620 can be defined by three sections, distal taper wall 624, medial working length 626, and proximal taper wall 628. As shown in FIG. 6, balloon 618 is positioned, in one embodiment, such that working length 620 is positioned adjacent a length of lesion 606. In one embodiment, proximal taper wall 628 and distal taper wall 634 can taper at any suitable angle, θ, typically between about 10° to less than about 90°, when balloon 618 is in the expanded configuration.

Distal taper wall 624, medial working length 626, and proximal taper wall 628 may be bound together by seams or be made out of a single seamless material. Balloon 618 may be made from any suitable material, including, but not limited to, polymers and copolymers of polyolefins, polyamides, polyesters and the like. The specific material employed must be mutually compatible with the fluids employed in conjunction with balloon 618 and must be able to stand the pressures that are developed within balloon 618. In one embodiment, balloon wall 620 may have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, ability to form a recess within the material and accommodate a fluid within the recess and low susceptibility to defect caused by handling. By way of example, and not limitation, the thickness may be in the range of about 10 µm to about 30 µm, the diameter of balloon 218 in the expanded configuration may be in the range of about 2 mm to about 10 mm, and the length may be in the range of about 3 mm to about 40 mm. It is appreciated that the specific specifications may vary depending on the procedure for which balloon 618 is to be used and the anatomy and size of the target lumen in which balloon 618 is to be inserted. Still further, the thickness may be varied depending upon a desired depth of a recess formed within the material as will be described in more detail below.

Balloon 618 may be expanded by the introduction of the liquid into inflation cannula 614. Liquids containing treatment or diagnostic agents (contrast) may also be used to inflate balloon 618. In one embodiment, balloon 618 may be made of a material that is permeable to such therapeutic or diagnostic liquids. To inflate balloon 618, the fluid may be supplied into inflation lumen 614 at a predetermined pressure, for example, between about one and 20 atmospheres.

Overlying working length 626 of balloon 618 is stent 630. In this embodiment, stent 630 is mounted on a distal portion of catheter assembly 608. Stent 630 may be a tubular stent such as that described in reference to FIG. 2 including a plurality of radially expandable cylindrical elements such as a plurality of struts disposed generally coaxially and interconnected by connecting elements and a plurality of links disposed between adjacent struts. Stent 630 may be expanded upon inflation of underlying balloon 618 at a pressure as described in reference to FIG. 2 such that stent 438 opposes the inner wall of artery 600 over lesion 606 but need not support vessel 600 or apply excessive force to open up vessel 600. It is contemplated that stent 630 may be a bare stent (non-coated), drug eluting stent (DES) or a coated stent.

Returning to balloon 618 of catheter assembly 608, balloon 618 has a plurality of delivery outlets 634 disposed along working length 626 of balloon 618. Some of delivery outlets 634 are positioned such that they coincide with openings 632 between the struts and links of stent 630 when balloon 618 is inflated while others are aligned with the struts and link of the stent. In this aspect, some of delivery outlets 634 populate openings 632 between struts and links of stent 630 when balloon 618 is expanded. Alternatively, delivery outlets 634 may be disposed anywhere along working length 626 of balloon 618 so long as they coincide with at least some of openings 632.

In one embodiment, delivery outlets 634 may be needles 634A extending from working length 626 of wall 620. In one embodiment, needles 634A may be substantially similar to, and attached to balloon wall 620, as described with respect to FIG. 2. Delivery outlets 634 may further include outlets which, instead of extending from wall 620, are formed within wall 620. Such delivery outlets 634 may include recesses 634B dimensioned to accommodate and release an amount of fluid including, for example, a treatment agent from wall 620. Recesses 634B may be formed in balloon wall 620 by standard techniques, including, but not limited to, plasma techniques, sand blasting, salt bleaching or etching.

Recesses 634B may have dimensions which vary depending upon factors such as the material used for the balloon, the type of treatment agent released from the recess and the desired dose to be released from recess 634B. It is further contemplated that a shape of recesses 634B may vary and include, for example, a discoid or a square shape. For example, recess 634B may have a discoid shape with a diameter of from about 5 µm to about 100 µm and a depth of from about two percent (%) to about 60% of a thickness of balloon wall 620. Still further, the dimensions and number of recesses formed in balloon wall 620 can vary depending upon an amount of treatment agent desired to be delivered to a vessel region. For example, in some embodiments, the density or fraction of the area of a surface of balloon wall 620 covered by recesses 634B is about 5% to about 80% of the overall area of the surface of balloon wall 620. The amount of treatment agent delivered is proportional to a volume fraction of recesses 634B within balloon wall 620. It is further contemplated that the number and dimensions of recesses 634B can be modified to any degree so long as the modification does not alter the mechanical properties of balloon 618 or compromise delivery of a treatment agent.

A membrane 636 may overlay an opening adjacent vessel lumen 604. In this aspect, a fluid, such as a solution including a treatment agent, loaded into recess 634B may be retained within recess 634B while catheter assembly 608 is being inserted into vessel 604. Membrane 636 may be made of a material that swells when balloon 618 is expanded and eventually dissolves or bursts as balloon 618 expands. In this aspect, a material of membrane 636 may be any dissolvable material compatible with the treatment agent to be delivered and safe for dissolution within a blood stream. Representatively, membrane 636 may be made of a hydrophilic material, including but not limited to, a polyvinyl acetate (PVA). In one embodiment, a treatment agent may be loaded into recess 634B and then a membrane 636 may be formed over each opening of recess 634B. Alternatively, a material having recesses with membranes already covering the openings may be formed into balloon wall 620 and the treatment agent loaded into the recesses by, for example, injecting an amount of treatment agent though membrane 636 and into each recess 634B.

Recesses 634B may be formed within regions of balloon 620 between needles 634A. In this aspect, as a fluid, such as a treatment agent, is administered through inflation lumen 614 and into balloon 618, balloon 618 expands forcing the treatment agent to be released from needles 634A and recesses 634B as membranes 636 dissolve or burst. Accordingly, the treatment agent may be released into regions of lesion 606 exposed through openings 632 between struts of stent 630 while simultaneously being released adjacent an outer surface of lesion 606 from recesses 634B. In this aspect, both local treatment at the site of lesion 606 and regional treatment of a diseased vessel region, for example, downstream, may be achieved. It is further contemplated that needles 634A may be omitted and recesses 634B aligned with openings 632.

FIG. 7 shows a cross-sectional side view of catheter assembly 608 at line C-C' of FIG. 6. FIG. 7 illustrates stent 630 having struts overlying balloon 618. Dimensions of the struts of stent 630 are substantially similar to those described in reference to FIG. 3. Balloon 618 is shown in an expanded configuration having guidewire cannula 612, guidewire 616 and inflation cannula 614 disposed therein. As shown in FIG. 7, needles 634A are positioned along balloon 618 such that when balloon 618 is in an expanded configuration, needles 634A extend through openings 632 between the struts of stent 630. Recesses 634B having membranes 636 are further shown formed within regions of balloon wall 620 between needles 634A. In this aspect, needles 634A and recesses 634B may deliver a fluid, such as a treatment agent, to a lesion or vessel wall concentrically outward from stent 630. Although eight needles 634A and eight recesses 634B are illustrated in FIG. 7, it is contemplated that any number of needles and recesses extend along working length 626 of balloon 618. Still further, needles 634A and recesses 634B may be arranged along balloon 618 in any manner so long as a sufficient number of the needles and recesses release a treatment agent to regions of lesion 606 exposed through openings 632 of stent 630. For example, in some embodiments, half of needles 634A extending from balloon 618 and half of the recesses 634B may be positioned beneath stent 630 and another half of needles 634A and half of the recesses 634B may be positioned within openings 632 when balloon 618 is expanded.

Figures 8, 9:
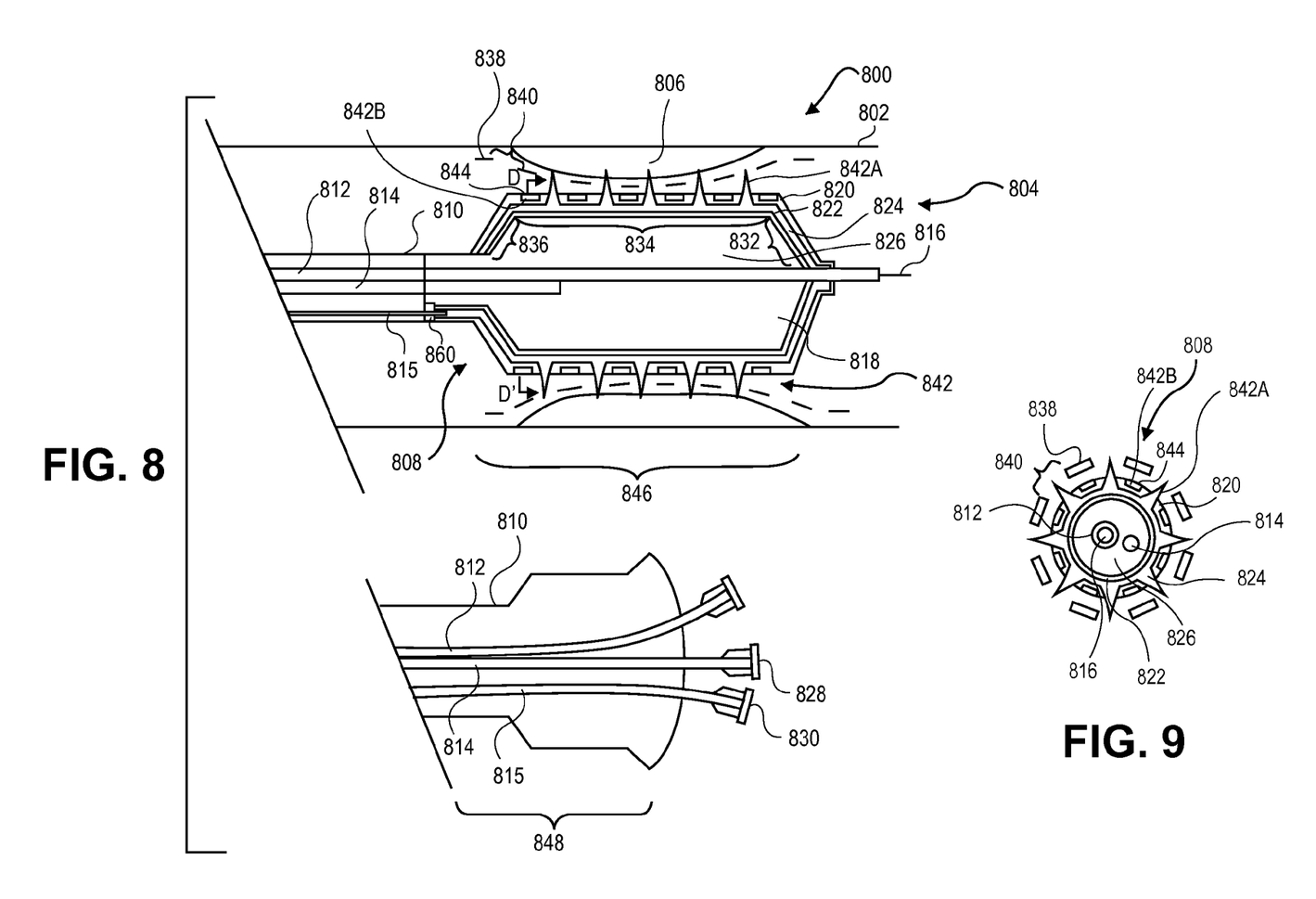
FIG. 8 shows a cross-sectional schematic side view of a blood vessel including a lesion and having another embodiment of a device including a balloon and a stent disposed in the blood vessel.
FIG. 9 shows a cross-sectional side view of the device of FIG. 8 through line D-D'.

FIG. 8 shows a cross-sectional schematic side view of a blood vessel including an occlusion and having another embodiment of a device including a balloon and a stent disposed in the blood vessel. Referring to FIG. 8, blood vessel 800 includes blood vessel wall 802 defining lumen 804. Disposed within blood vessel 800 is a lesion 806.

FIG. 8 shows a device disposed within lumen 804 defined by blood vessel wall 802. In one embodiment, the device may include a stent 838 and a balloon catheter assembly 808. FIG. 8 shows a distal portion 846 and a proximal portion 848 of catheter assembly 808. Proximal portion 848 may be external to blood vessel 800 and to the patient. Representatively, stent 838 and catheter assembly 808 may be inserted through a femoral artery and through, for example, a guide catheter and with the aid of a guidewire to a location in the vasculature of a patient. That location may be, for example, a coronary artery. In one embodiment, stent 838 may be mounted on a balloon 818 of catheter assembly 808 during insertion. FIG. 8 shows distal portion 846 of catheter assembly 808 positioned adjacent lesion 806. In this aspect, catheter assembly 808 is positioned adjacent the treatment region. Catheter assembly 808 includes primary cannula 810 having a lumen therethrough, the lumen sized to contain at least a guidewire cannula 812, a first inflation cannula 814 and a second inflation cannula 815. Each of guidewire cannula 812, first inflation cannula 814 and second inflation cannula 815 has a lumen therethrough. A lumen of guidewire cannula 812 accommodates guidewire 816. Catheter assembly 808 also includes balloon 818 connected at a proximal end to primary cannula 810 and a distal end to guidewire cannula 812. A distal end of first inflation cannula 814 is disposed within balloon 818 such that balloon 818 is in fluid communication with first inflation cannula 814 formed within primary cannula 810.

In the embodiment shown in FIG. 8, balloon 818 is a double walled balloon including an outer balloon wall or membrane 820 and an inner balloon wall or membrane 822 having similar specifications and dimensions to that described in reference to FIG. 4. In this aspect, an outer reservoir 824 is formed between outer wall 820 and inner wall 822 and an inner reservoir 826 separate from outer reservoir 824 is defined by inner wall 822. Outer wall 820 and inner wall 822 are attached at one end to a cuff 860 to help maintain a separation between outer wall 820 and inner wall 822 so that a distal end of second inflation cannula 815 may be inserted between walls 820, 822 and terminate within outer reservoir 824. Cuff 860 may be substantially similar to cuff 460 described in reference to FIG. 4. A distal end of second inflation cannula 815 terminates within outer reservoir 824 and the distal end of first inflation cannula 814 terminates within inner reservoir 826 of balloon 818. In this aspect, balloon 818 is selectively inflatable to expand from a collapsed configuration to a desired and controlled expanded configuration. Balloon 818 can be selectively expanded by supplying a fluid into first inflation cannula 814 at a predetermined rate of pressure through inflation port 828. Alternatively, balloon 818 can be selectively expanded by supplying a fluid into second inflation cannula 815 at a predetermined rate of pressure through inflation port 830. In still further embodiments, balloon 818 may be selectively expanded by simultaneously supplying a first fluid into first inflation cannula 814 and a second fluid into second inflation cannula 815 at predetermined rates of pressure through fluid ports 828 and 830 respectively. The first fluid and the second fluid may be the same or they may be different fluids as deemed desirable.

Balloon 818 is selectively deflatable, after inflation, to return to the collapsed configuration or a deflated profile. In one embodiment, balloon wall 820, 822 can be defined by three sections, distal taper wall 832, medial working length 834, and proximal taper wall 836. Balloon 818 of catheter assembly 808 is positioned, in one embodiment, such that working length 834 is positioned adjacent a length of lesion 806. In one embodiment, proximal taper wall 836 and distal taper wall 832 can taper at any suitable angle θ, typically between about 10° to less than about 90°, when balloon 818 is in the expanded configuration.

Distal taper wall 832, medial working length 834, and proximal taper wall 836 of balloon wall 820 may be bound together by seams or be made out of a single seamless material. Similarly, distal taper wall 832, medial working length 834, and proximal taper wall 836 of balloon wall 822 may be bound together by seams or be made out of a single seamless material. Wall 820 and wall 822 may be connected at proximal ends to primary cannula 810 and distal ends to guidewire cannula 812. Balloon 818 may be made from any suitable material, including, but not limited to, polymers and copolymers of polyolefins, polyamides, polyesters and the like. The specific material employed must be mutually compatible with the fluids employed in conjunction with balloon 818 and must be able to stand the pressures that are developed within balloon 818. Balloon walls 820, 822 may be of the same or different materials. In one embodiment, balloon wall 820, 822 may have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. Balloon 818 specifications may include a thickness, outer diameter and length similar to that described in reference to FIG. 4. It is appreciated that the specific specifications may vary depending on the procedure for which balloon 818 is to be used and the anatomy and size of the target lumen in which balloon 818 is to be inserted. For example, in one embodiment, it may be desirable to have different expansion characteristics for inner reservoir 826 and outer reservoir 824. In this aspect, inner wall 822 and outer wall 820 may have different thicknesses or be made of different materials. Still further, the thickness may be varied depending upon a desired depth of a recess formed within the material as will be described in more detail below Balloon 818 may be expanded by the introduction of the liquid into first inflation cannula 814 or second inflation cannula 815. Liquids containing treatment or diagnostic agents (e.g. contrast) may also be used to inflate balloon 818. In one embodiment, balloon 818 may be made of a material that is permeable to such therapeutic or diagnostic liquids. To inflate balloon 818, the fluid may be supplied into first inflation lumen 814 or second inflation lumen 815 at a predetermined pressure, for example, between about one and 20 atmospheres.

Overlying working length 834 of balloon 818 is stent 838. In this embodiment, stent 838 is mounted on a distal portion of catheter assembly 808. Stent 838 may be a tubular stent such as that described in reference to FIG. 2 including a plurality of radially expandable cylindrical elements such as a plurality of struts disposed generally coaxially and interconnected by connecting elements and a plurality of links disposed between adjacent struts. Stent 838 may be expanded upon inflation of underlying balloon 618 at a pressure as described in reference to FIG. 2 such that stent 838 opposes the inner wall of artery 800 over lesion 806 but need not support vessel 800 or apply excessive force to open up vessel 800. It is contemplated that stent 838 may be a bare stent (non-coated), drug eluting stent (DES) or a coated stent.

Returning to balloon 818 of catheter assembly 808, balloon 818 has a plurality of delivery outlets 842 disposed along working length 834 of balloon 818. As illustrated in FIG. 8, some of delivery outlets 842 are positioned such that they coincide with openings 840 between the struts and links of stent 838 when balloon 818 is inflated. In one embodiment, delivery outlets 842 may be needles 642A extending from wall 820 of balloon 818. In one embodiment, needles 842A may be substantially similar to and secured to balloon wall 820 as described with respect to FIGS. 2-7. Delivery outlets 842 may further be recesses 842B disposed within wall 820 of balloon 818 for accommodating a fluid including, for example, a treatment agent. Recesses 842B may be formed in outer balloon wall 820 by standard techniques, including, but not limited to, plasma techniques, sand blasting, salt bleaching or etching. Recesses 842B may have dimensions similar to the recesses discussed in regard to FIG. 6. Representatively, recess 842B may have a diameter of from about 10 μm to about 100 μm and a depth of from about ten percent (%) to about 50% of a thickness of balloon wall 820.

A membrane 844, similar to that discussed in regard to FIG. 6 may overlay an opening of each recess 842B adjacent vessel lumen 804. In this aspect, a fluid, such as a solution including a treatment agent, loaded into recess 842B may be retained within recess 842B while catheter assembly 808 is being inserted into vessel 804. Once assembly 808 is in position, inner reservoir 826 or outer reservoir 824 may be expanded as previously described such that a treatment agent loaded into recess 842B may be released.

FIG. 9 shows a cross-sectional side view of the device of FIG. 8 through line D-D'. FIG. 9 illustrates stent 838 having struts overlying balloon 818. Dimensions of the struts of stent 838 are substantially similar to those described in reference to FIG. 3. Balloon 818 is shown in an expanded configuration having guidewire cannula 812, guidewire 816 and first inflation cannula 814 disposed therein. Outer wall 820 and inner wall 822 of balloon 818 are further shown. Inner reservoir 826 is defined by inner wall 822 and outer reservoir 824 is defined by inner wall 822 and outer wall 820 of balloon 818. As shown in FIG. 9, needles 842A are positioned along an outer wall 820 of balloon 818 such that when balloon 818 is in an expanded configuration, needles 842A extend through openings 840 between the struts of stent 838. Recesses 842B having membranes 844 are further shown formed within regions of outer balloon wall 820 between needles 842A. In this aspect, needles 842A and recesses 842B may deliver a fluid, such as a treatment agent, to a lesion or vessel wall concentrically outward from stent 838. Although eight needles 842A and eight recesses 842B are illustrated in FIG. 9, it is contemplated that any number of needles and recesses extend along working length 834 of balloon 818. Still further, the needles and recesses may be arranged along balloon 818 in any manner so long as a sufficient number of the needles and recesses release a treatment agent to desired vessel regions. of lesion 806 exposed through openings 840 of stent 838.

Figure 10:
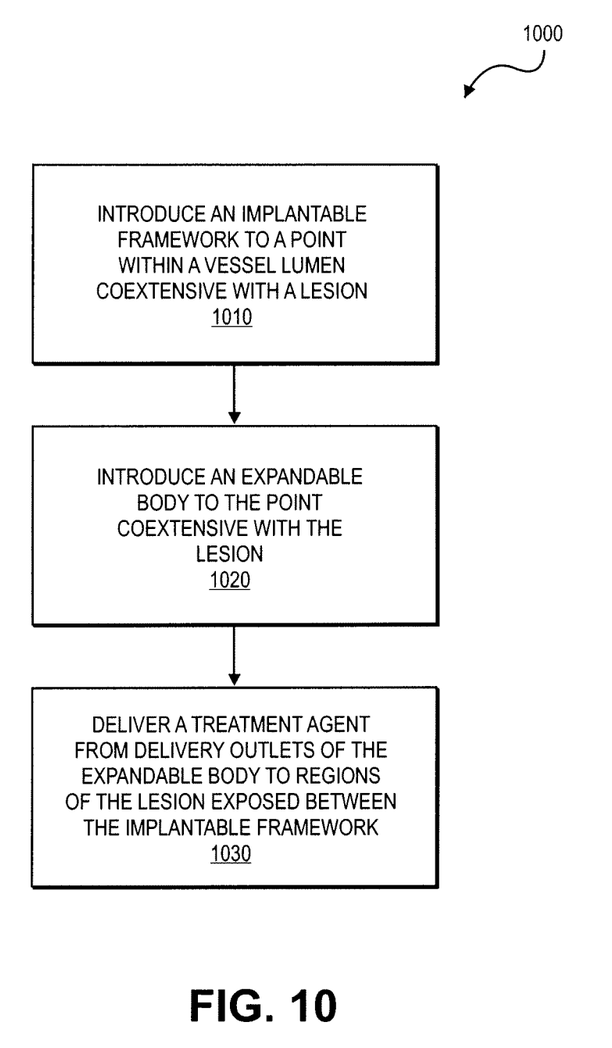
FIG. 10 is a flowchart detailing a method for delivering a treatment agent to a lesion using a delivery device.

FIG. 10 is a flowchart detailing a method 1000 for delivering a treatment agent to a lesion using a delivery device. In one embodiment, an implantable framework is introduced to a point within a vessel lumen coextensive with a lesion (block 1010). The implantable framework may be a stent as previously described. The stent may cover the lesion. In this aspect, some portions of the lesion may be covered by, for example, stent struts while other regions of the lesion are exposed between the framework. An expandable body is introduced to the point coextensive with the lesion (block 1020). The expandable body may be a balloon including an outer wall with at least one delivery outlet, for example, a needle or a recess disposed along the working length of the outer wall. A treatment agent may be loaded into the delivery outlet as previously described. Upon expansion of the balloon, the treatment agent may be delivered from the delivery outlet to regions of the lesion exposed between the framework (block 1030). In this aspect, where the delivery outlets are needles, the needles puncture the vessel lesion to deliver the treatment agent instead of healthy vessel regions.

In the preceding detailed description, specific embodiments are presented. Those embodiments include apparati (devices) and methods for regionally and locally treating desired treatment sites. It will, however, be evident that various modifications and changes may be made thereto without departing from the broader spirit and scope of the claims. For example, other implantable medical devices may be used in conjunction with a balloon for delivering a treatment agent to a desired treatment site. The specification and drawings are, accordingly, to be regarded in an illustrative rather than a restrictive sense.

What is claimed is:

1. An apparatus comprising:
   an expandable body suitable for insertion into a blood vessel and capable of expanding from a first diameter to a second diameter in response to an inflation pressure, the expandable body comprising:
      an outer wall having a working length,
      a plurality of needles extending from the outer wall, each of the needles having a lumen in fluid communication with an aperture formed in the outer wall, and
      a plurality of recesses extending through only a portion of the outer wall, the recesses dimensioned to hold a treatment agent;
   a delivery cannula coupled to the expandable body, the delivery cannula in fluid communication with each aperture such that a fluid introduced through the delivery cannula to expand the expandable body from the first diameter to the second diameter is delivered through the needles; and
   a stent having struts and openings between the struts, the stent overlying the outer wall such that the needles align with the openings and the recesses align with the struts,
   wherein the first diameter comprises a collapsed configuration and the second diameter comprises an expanded configuration, wherein the expanded configuration advances the needles through the openings to place the needles in contact with portions of a lesion exposed through the openings and releases the treatment agent into the blood vessel.

2. The apparatus of claim 1 wherein the expandable body is a balloon.

3. The apparatus of claim 1 wherein the fluid comprises a treatment agent and the expandable body is coupled to a distal portion of the delivery cannula, the delivery cannula having a length dimension suitable to be positioned from a first externally accessible site of a patient to a position within the blood vessel by way of a percutaneous transluminal route.

4. The apparatus of claim 1 wherein the expandable body further comprises:
   an inner wall wherein an outer reservoir is defined by the outer wall and the inner wall and a separate inner reservoir is defined by the inner wall.

5. The apparatus of claim 1 wherein the needles are flexible.

6. The apparatus of claim 1 wherein a membrane covers an opening of each recess, the membrane having a property to rupture in response to one of expansion of the outer wall or biological conditions within the blood vessel, and wherein the treatment agent is released from the recess in response to the membrane rupture.

7. A method comprising:
   introducing an expandable body having a stent crimped thereon to a point within a vessel lumen coextensive with a lesion, the expandable body comprising:
      an outer wall having a working length,
      a plurality of needles extending from the outer wall, each of the needles having a lumen in fluid communication with an aperture formed in the outer wall, and
      a plurality of recesses extending through only a portion of the outer wall, the recesses dimensioned to hold a treatment agent, and
      the stent comprising struts and openings between the struts, wherein the needles align with the openings and the recesses align with the struts;
   after introducing the expandable body, inflating the expandable body from a first diameter having a collapsed configuration to a second diameter having an expanded configuration, wherein the expanded configuration advances the needles through the openings to place the needles in contact with portions of a lesion exposed through the openings;
   delivering a fluid used to inflate the expandable body from the first diameter to the second diameter from the needles to the lesion; and
   releasing the treatment agent from the recesses into the blood vessel.

8. The method of claim 7 wherein the expandable body is a balloon.

9. The method of claim 7 further comprising:
   a delivery cannula wherein the expandable body is coupled to a distal portion of the delivery cannula for administering the fluid therein, the delivery cannula having a length dimension suitable to be positioned from a first externally accessible site of a patient to a position within the blood vessel by way of a percutaneous transluminal route.

10. The method of claim 7 wherein the expandable body further comprises:
    an inner wall wherein an outer reservoir is defined by the outer wall and the inner wall and a separate inner reservoir is defined by the inner wall.

11. The method of claim 7 wherein the needles are flexible.

12. The method of claim 7 wherein a membrane covers an opening of each recess, and further comprising rupturing the membrane in response to the inflating, and wherein the releasing is in response to the rupturing.

13. The method of claim 7 wherein the fluid comprises a combination of a local treatment agent and a regional treatment agent.

14. The method of claim 13 wherein the local treatment agent is selected from the group consisting of paclitaxel and everolimus.

15. The method of claim 13 wherein the regional treatment agent is ApoA1.

16. The method of claim 7 wherein the fluid is delivered as a mixture including a treatment agent and a contrast agent.

17. A kit comprising:
    a delivery cannula having a dimension suitable for insertion into a blood vessel toward a lesion and an expandable body coupled thereto, the expandable body comprising an outer wall having a working length capable of expanding from a first diameter to a second diameter in response to an inflation pressure, a plurality of needles extending from the outer wall, each of the needles having a lumen in fluid communication with an aperture formed in the outer wall, the delivery cannula in fluid communication with the expandable body and the needles such that a fluid introduced through the delivery cannula to expand the expandable body from the first diameter to the second diameter is delivered through the needles to the lesion, and a plurality of recesses extending through only a portion of the outer wall, the recesses dimensioned to hold a treatment agent;
    a stent overlying the outer wall, the stent having a first outer diameter suitable for insertion into the blood vessel and a second outer diameter to retain a perimeter similar to that of the blood vessel, the stent having struts and openings between the struts, wherein the needles align with the openings and the recesses align with the struts; and
    a fluid for delivery to a treatment site,
    wherein the first diameter comprises a collapsed configuration and the second diameter comprises an expanded configuration, wherein the expanded configuration advances the needles through the openings to place the needles in contact with portions of the lesion and releases the treatment agent into the blood vessel.

18. The kit of claim 17 wherein the expandable body is a balloon.

19. The kit of claim 17 wherein the expandable body further comprises an inner wall concentrically inward from the outer wall, wherein an outer reservoir is defined by the outer wall and the inner wall and a separate inner reservoir is defined by the inner wall.

20. The kit of claim 17 wherein the needles are flexible.

21. The kit of claim 17 wherein a membrane covers an opening of each recess, the membrane having a property to rupture in response to one of expansion of the outer wall or biological conditions within the blood vessel, and wherein the treatment agent is released from the recess in response to the membrane rupture.

22. The kit of claim 17 wherein the fluid comprises a combination of a local treatment agent and a regional treatment agent.

23. The kit of claim 22 wherein the local treatment agent is selected from the group consisting of paclitaxel and everolimus.

24. The kit of claim 22 wherein the regional treatment agent is ApoA1.

25. The kit of claim 17 wherein the fluid is delivered as a mixture including a treatment agent and a contrast agent.

* * * * *